Figure 1:
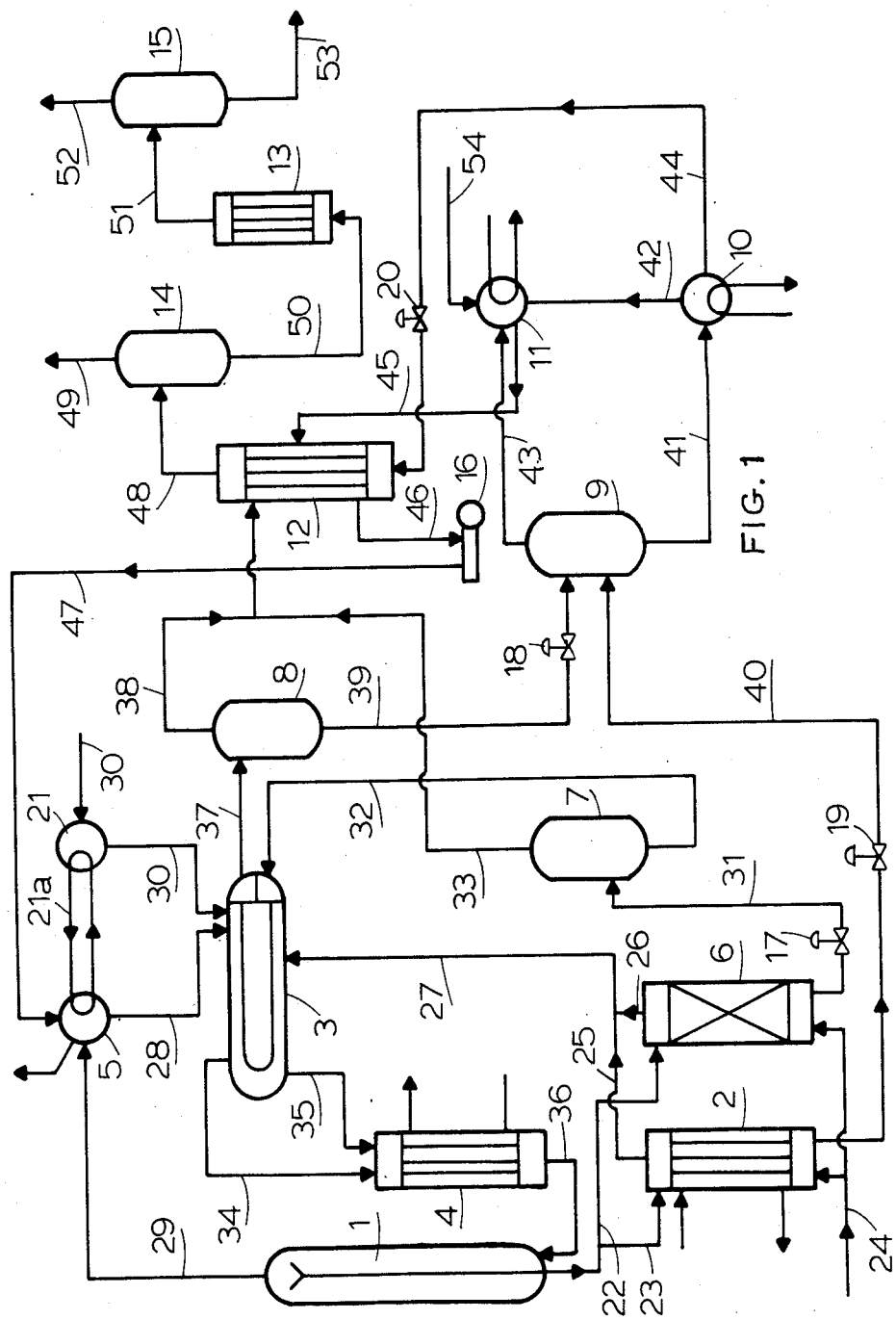

United States Patent [19]

Baenens

[11] Patent Number: 4,801,746
[45] Date of Patent: Jan. 31, 1989

[54] PROCESS FOR THE PREPARATION OF UREA

[75] Inventor: Victor E. A. Baenens, Maasmechelen, Belgium

[73] Assignee: Stamicarbon B.V., AC Geleen, Netherlands

[21] Appl. No.: 895,429

[22] Filed: Aug. 11, 1986

[30] Foreign Application Priority Data

Aug. 12, 1985 [NL] Netherlands ............... 8502228

[51] Int. Cl.$^4$ ............... C07C 126/00; C07C 126/02
[52] U.S. Cl. ............... 564/70; 564/71; 564/72; 564/67
[58] Field of Search ............... 564/70, 72, 71, 67

[56] References Cited

U.S. PATENT DOCUMENTS

| | | | |
|---|---|---|---|
| 3,406,201 | 10/1968 | Baumann et al. | 564/70 |
| 3,936,500 | 2/1976 | Kaasenbrood et al. | 564/70 |
| 4,138,434 | 2/1979 | Lagana et al. | 564/70 X |
| 4,314,077 | 2/1982 | Zardi et al. | 564/70 |
| 4,354,040 | 10/1982 | Inoue et al. | 564/70 X |

FOREIGN PATENT DOCUMENTS 190290  7/1961  U.S.S.R. ............... 564/70

OTHER PUBLICATIONS

Kirk–Othmer, "Encyclopedia of Chemical Technology", vol. 21, pp. 37 to 51 (1970).

Primary Examiner—Floyd D. Higel
Attorney, Agent, or Firm—Cushman, Darby & Cushman

[57] ABSTRACT

Process for the preparation of urea in which a urea synthesis solution containing carbamate and free ammonia is formed in a high-pressure part in a synthesis zone at an $NH_3/CO_2$ molar ratio of up to 4:1, a temperature of at least 175° C. and the corresponding pressure, a portion of the carbamate is decomposed in a first decomposition stage at synthesis pressure or lower pressure by a stripping treatment with carbon dioxide while heat is being supplied, and the gas mixture thus obtained is at least in part condensed and the condensate and the non-condensed portion of the gas mixture, if any, are returned to the synthesis zone, a further portion of the carbamate still present is decomposed in at least two further decomposition stages and the gas mixture formed is separated, in the first of the further decomposition stages a pressure of 12-30 bar being maintained and heat being supplied and in the second of the further decomposition stages a lower pressure being maintained, and the remaining urea-containing solution is processed further by evaporation to a concentrated urea solution and, if desired, solid urea.

In the first decomposition stage a portion of the urea synthesis solution is subjected to a stripping treatment with carbon dioxide while heat is being supplied, and the remaining portion of the urea synthesis solution is countercurrently contacted with carbon dioxide under adiabatic conditions. The gas mixtures obtained in both operations are at least in part condensed in a first condensation zone. The solution obtained in the treatment of the urea synthesis solution with carbon dioxide under adiabatic conditions is supplied to the first of the further decomposition stages and the stripped urea synthesis solution to the second of the further decomposition stages.

4 Claims, 1 Drawing Sheet

PROCESS FOR THE PREPARATION OF UREA

The invention relates to a process for the preparation of urea from ammonia and carbon dioxide.

When ammonia and carbon dioxide are introduced into a synthesis zone at a suitable pressure (for instance 125-350 atm) and at a suitable temperature (for instance 170°-250° C.), first ammonium carbamate is formed according to the reaction:

$$2NH_3 + CO_2 \rightarrow H_2N-CO-ONH_4$$

From the ammonium carbamate formed, urea is subsequently formed through dehydration according to the reversible reaction:

$$H_2N-CO-ONH_4 \rightleftharpoons H_2N-CO-NH_2 + H_2O$$

The degree to which the conversion to urea takes place depend, inter alia, on the temperature and the ammonia excess used. As reaction product, a solution is obtained that consists mainly of urea, water, ammonium carbamate and free ammonia. The ammonium carbamate and the ammonia are to be removed from the solution; mostly, they are returned to the synsthesis zone. This synthesis zone may consist of separate zones for carbamate and urea formation, but these zones may also be accommodated in one apparatus.

One process for the preparation of urea that has found wide use in practical applications is described in European Chemical News, Urea Supplement of Jan. 17, 1969, pages 17-20. In said process, the urea synthesis solution formed at high temperature and pressure in the synthesis zone is subjected to a stripping treatment at synthesis pressure by countercurrently contacting the solution with gaseous carbon dioxide while supplying heat, so that the larger part of the carbamate present in the solution decomposes into ammonia and carbon dioxide, and these decomposition products are in gaseous form expelled from the solution, and discharged together with a minor amount of water vapour and the carbon dioxide used for stripping. The heat required for the stripping treatment is obtained by condensation of high-pressure steam of 15-25 bar, on the shell side of the tubes of the vertical heat exchanger in which stripping takes place. The gas mixture obtained in the stripping treatment passes to a first condensation zone and is for the larger part condensed and absorbed in an aqueous solution originating from the further treatment of the urea-containing solution, upon which both the aqueous carbamate solution thus formed and the non-condensed gas mixture are sent to the synthesis zone for urea formation. Here, the heat required for the conversion of carbamate into urea is obtained by further condensation of the gas mixture.

The stripped urea synthesis solution is subsequently expanded to a low pressure of, for instance, 3-6 bar and heated by means of steam so as to remove the ammonia and carbon dioxide still partly present as carbamate from the stripped urea solution. The gas mixture obtained in these operations, which also contains water vapour, is condensed and absorbed in an aqueous solution in a second condensation zone, which is operated at low pressure, and the resulting dilute carbamate solution is returned to the high-pressure section of the urea synthesis and eventually introduced into the synthesis zone. The remaining urea-containing solution is reduced further in pressure and is worked up to a urea solution or melt that may be processed to solid urea. To this end, the aqueous urea solution is usually evaporated in two evaporation stages and the urea melt thus obtained is processed to granules, or the urea solution is crystallized. The gases obtained during evaporation or crystallization, which besides water vapour contain, inter alia, ammonia, carbon dioxide and entrained fine urea droplets, are condensed, yielding so-called process condensate. A portion of the process condensate is used as absorption agent for the gas mixture in the second condensation zone. The remainder can be treated with high-pressure steam for decomposition into ammonia and carbon dioxide of urea contained in it and recovery of these decomposition products together with the ammonia and carbon dioxide already present as such.

It has already been proposed to incorporate an additional decomposition stage in such a process in which further amounts of carbamate, that are still present in the stripped urea synthesis solution, are decomposed at a pressure of 12-25 kg/cm$^2$ (see U.S. Pat. No. 4,354,040). A drawback of such an additional decomposition stage is that the molar ratio of the ammonia and carbon dioxide not converted into urea in the urea-containing solution discharged from this additional decomposition stage is relatively high. As a consequence, this ratio will also be relatively high in the gas mixture formed on decomposition of carbamate still present in the further decomposition stages.

For complete condensation into a crystal-free carbamate solution of such gas mixtures, considerable amounts of water or water-containing absorbents are required. If, as is done in the process described, a portion of the fresh carbon dioxide required in the synthesis is supplied to the last decomposition stage, the gas mixture obtained in this stage is given an NH$_3$/CO$_2$ molar ratio that is more favourable for complete condensation under the prevailing conditions. In this condensation, however, the heat of condensation is released at the low temperature level belonging to this decomposition stage, as a consequence of which there are hardly any possiblities for efficient use of the heat released, necessitating its discharge by means of cooling water. Another drawback is that the carbon dioxide supplied to the last decomposition stage is no longer available for the stripping treatment in the high-pressure part, so that a larger amount of carbamate remains in the stripped urea synthesis solution, which must be removed in the following decomposition stages.

The object of the invention is to provide a process for the preparation of urea which avoids the above-mentioned drawbacks. According to the invention this can be achieved if only a portion of the urea synthesis solution is treated in an additional decomposition stage at 12-30 bar, without prior heat supply. It has been found that, if subsequently further amounts of carbamate still present, both in the portion treated in the additional decomposition stage and in the portion of the solution that originates from the stripping treatment, are decomposed at lower pressures than the pressure in the additional decomposition stage, without supply of fresh carbon dioxide in this stage a gas mixture is obtained the NH$_3$/CO$_2$ ratio of which is such that the gas mixture can be condensed without addition of excessively large amounts of water.

The invention therefore relates to a process for the preparation of urea in which:

a urea synthesis solution containing carbamate and free ammonia is formed in a high-pressure part in a synthesis zone at an $NH_3/CO_2$ molar ratio of up to 4:1, a temperature of at least 175° C. and the corresponding pressure, a portion of the carbamate is decomposed in a first decomposition stage at synthesis pressure or lower pressure by a stripping treatment with carbon dioxide while heat is being supplied, and the gas mixture thus obtained is at least in part condensed and the condensate and the non-condensed portion of the gas mixture, if any, are returned to the synthesis zone, a further portion of the carbamate still present is decomposed in at least two further decomposition stages and the gas mixture formed is separated, in the first of the further decomposition stages a pressure of 12–30 bar being maintained and heat being supplied and in the second of the further decomposition stages a lower pressure being maintained, and the remaining urea-containing solution is processed further by evaporation to a concentrated urea solution and, if desired, solid urea.

The process according to the invention is characterized in that in the first decomposition stage a portion of the urea synthesis solution is subjected to a stripping treatment with carbon dioxide while heat is being supplied, and the remaining portion of the urea synthesis solution is contercurrently contacted with carbon dioxide under adiabatic conditions, after which the gas mixtures obtained in both operations are at least in part condensed in a first condensation zone, the solution obtained in the treatment of the urea synthesis solution with carbon dioxide under adiabatic conditions is supplied to the first of the further decomposition stages and the stripped urea synthesis solution to the second of the further decomposition stages.

Preferably, 50–70 wt.% of the urea synthesis solution is subjected to the stripping treatment with carbon dioxide while heat is being supplied, and 50–30 wt.% to the treatment with carbon dioxide under adiabatic conditions. The amount of carbon dioxide required in the urea process is divided between both treatment stages in virtually the same proportion.

As a result of the treatment with carbon dioxide under adiabatic conditions of a portion of the urea synthesis solution, the latter's ammonia content is reduced and the carbon dioxide content increased. A portion of the carbamate still present in it is decomposed by heating in the first of the further decomposition stages at a pressure of 12–30 bar, after the gas mixture formed on expansion to a pressure of 12–30 bar has been separated. Heating can be effected by means of, for instance, steam. By preference, heating is effected by heat exchange with the condensing gas mixture at synthesis pressure in the first condensation zone. If the conditions in the first condensation zone are chosen such that also a considerable amount of urea, for instance at least 30% of the equilibrium amount achievable under the reaction conditions, is formed from the carbamate formed in condensation, the heat will be released at such a temperature level that a considerable portion of the carbamate present in the solution can be decomposed into ammonia and carbon dioxide. As a rule, there will even be a surplus of heat. This heat can then be discharged in a second high-pressure condensation zone by means of boiler feed water, which is thereby converted into low-pressure steam of 4–9 bar. The gas mixture formed on carbamate decomposition as a result of heat exchange with the condensing gas mixture in the first condensation zone, can, for instance, be condensed together with the gas mixture obtained on expansion of the solution that has undergone the treatment with carbon dioxide under adiabatic conditions. As a result of the treatment of a portion of the urea synthesis solution with carbon dioxide under adiabatic conditions, the $NH_3/CO_2$ molar ratio in the gas mixture obtained in the first of the further decomposition stages in the 12–30 bar pressure range will be close to the value for the azeotropic condition, so that in condensation of this gas mixture the maximum attainable temperature is virtually reached.

By preference, this condensation is effected using the carbamate solution obtained on further processing of the stripped urea synthesis solution in a decomposition stage operating at a pressure of, for instance, 1–10 bar, which carbamate solution is first brought up to the prevailing pressre in the 12–30 bar pressure range by means of a pump. The heat of condensation can then be obtained at a level of 145°–110° C., which is substantially higher than in the process according to the abovementioned U.S. Pat. No. 4,354,040. The heat released in condensation can, for instance, be utilized by heat exchange with the urea solution to be evaporated. When this is effected by passing the urea solution to be evaporated countercurrent to the condensing gas mixture, the urea solution can, for instance, be concentrated at temperatures between 85° and 130° C. from a urea concentration of about 70 wt.% to about 95 wt.%. These values largely correspond with the concentration normally achieved in the first evaporation stage in the abovementioned process known from European Chemical News.

The solution remaining after separation of the gas mixture released in the first of the further decomposition stages, which has a relatively high $NH_3/CO_2$ molar ratio, is expanded to the pressure of the second of the further decomposition stages, for instance to a pressure of 1–10 bar. The solution that remains after the stripping treatment with heat supply and that has a relatively low $NH_3/CO_2$ ratio is also expanded to the pressure of the second of the further decomposition stages. If these solution are jointly subjected to a treatment for decomposition of further amounts of carbamate still present, for instance to heating by means of low-pressure steam, a gas mixture is obtained the $NH_3/CO_2$ molar ratio of which is such as to allow condensation without supply of excessively large amounts of water.

Compared with the known process, the process according to the invention has the advantage that only a relatively small amount of water is required for condensation of the gas mixtures obtained in the several decomposition stages, which has a favourable effect on the synthesis efficiency. Since no carbon dioxide is supplied to the low-pressure stage, the total amount of carbon dioxide required in the synthesis can be supplied to the stripping treatment and to the adiabatic treatment, so that the heat of condensation of this carbon dioxide can be put to efficient use, resulting in optimum efficiency of these treatments. For decomposition of the further amounts of carbamate and expulsion of the gas mixtures formed thereby in the decomposition stage operating at 12–30 bar, no additional amount of high-pressure steam is needed, as in the known process, but use is made of the heat content of the gas mixture obtained in the stripping treatment for this carbamate decomposition. Moreover, the heat content of the gas mixture from the decomposition stage operating at 12–30 bar can be utilized at a high temperature level in concentrating of the urea solution obtained to an approx. 95 wt.% solution by evaporation.

The invention will be elucidated with reference to the FIGURE without, however, being restricted thereto.

In the FIGURE, a synthesis zone is indicated by 1, a stripping zone by 2, a first and second high-pressure conensation zone by 3 and 4, respectively, and a scrubbing zone by 5. Shown as 6 is a contact zone for contacting urea synthesis solution with carbon dioxide. 7, 8 and 9 are devices for separating liquids and gases. 10 stands for a heat exchanger and 11 for a carbamate condensation zone operated at low pressure. The heating zone of the first and that of the second concentration stage are represented by 12 and 13, respectively, and the associated devices for separation of the water vapour formed in concentrating by 14 and 15, respectively. A carbamate pump is shown as 16, while 17, 18, 19 and 20 are expansion valves. Of the urea synthesis solution formed in urea synthesis zone 1 at a pressure of 125–250 bar, a temperature of 175°–220° C. and an $NH_3/CO_2$ molar ratio of 2.7–4.0, for instance 139 bar, 183° C. and an $NH_3/CO_2$ molar ratio of 3.2, which, besides urea and water, contains free ammonia and non-converted ammonium carbamate, an amount of 30–40 wt.%, for instance 44 wt.%, is supplied via 22 to contact zone 6, where it is contacted with carbon dioxide under adiabatic conditions. The remaining 50–70 wt.% of the urea synthesis solution is supplied to stripping zone 2, which is placed parallel with contact zone 6, through 23. Countercurrent to the urea synthesis solution, via 24 carbon dioxide, which has been compressed to synthesis pressure in a compression device not shown and to which, if desired, passivation air has been added, is supplied to stripping zone 2 and contact zone 6. Stripping zone 2 is preferably designed as a vertical shell-and-tube heat exchanger. The heat required in the stripping treatment is obtained by condensation of high-pressure steam of, for instance, 14–40 bar, in the shell side of the heat exchanger. To promote a good contact between the urea synthesis solution and the carbon dioxide gas, in contact zone 6 plates or packing materials can be installed. Likewise, the contact between gas and liquid can be effected in a falling liquid film. The gas mixture expelled from stripping zone 2, which besides ammonia and carbon dioxide contains equilibrium amounts of water vapour, is discharged via 25 with the carbon dioxide used for the stripping treatment. From contact zone 6, via 26 a gas mixture is discharged which contains the ammonia expelled from the urea synthesis solution, a portion of the carbon dioxide supplied and a small amount of water. The gas mixtures discharged via 25 and 26 are passed via 27 into the shell side of first condensation zone 3, represented in the FIGURE as a submerged condenser, horizontally placed, where they are partially condensed to a carbamate solution. Via 28, first condensation zone 3 is fed with a dilute carbamate solution, which is obtained in scrubbing ammonia and carbon dioxide out of the gas mixture containing inert gases that has been discharged from synthesis zone 1 via 29. The heat evolved in the formation of this dilute carbamate solution is utilized for preheating of the liquid ammonia supplied via 30. To this end, a heat exchanger 21 can be installed, in which the heat released in scrubbing zone 5 is transferred via a circuit 21a. The residence time of the reaction mixture in first condensation zone 3 is chosen such that in this zone also at least 30% of the equilibrium amount of urea achievable under the prevailing reaction conditions is formed from carbamate, so that a solution with, for instance, 20 wt.% urea is obtained. The heat released in first condensation zone 3 can be utilized for decomposition of carbamate present in the urea synthesis solution enriched with carbon dioxide. To this end, the solution discharged from contact zone 6 via 31 is expanded to a pressure of 12–30 bar, for instance 22 bar, in expansion valve 17, and the mixture formed is introduced into gas-liquid separator 7. The liquid phase thus formed, mainly an aqueous solution also containing biuret, ammonia and carbamate, is discharged via 32, and the gas phase, a mixture containing mainly ammonia, carbon dioxide and water vapour, via 33. The liquid phase discharged from gas-liquid separator 7 via 32 is subsequently passed, at a pressure equal to or lower than the pressure of gas-liquid separator 7, into heat exchange with the carbamate-urea solution being formed in first condensation zone 3, upon which a portion of the amount of carbamate present in the expanded solution is decomposed into ammonia and carbon dioxide. It is also possible to discharge the heat released in first condensation zone 3 by means of other process streams or with water, which is thereby converted into low-pressure steam. From first condensation zone 3, via 34 the non-condensed portion of the gas mixture fed to this zone, and via 35 the carbamate solution formed in this zone, is discharged and introduced into second high-pressure condensation zone 4. In this zone, further condensation to a carbamate solution of the gas mixture supplied via 34 takes place. The heat released thereby is discharged by means of water, which is thereby converted into low-pressure steam of 4–9 bar. The carbamate solution obtained in this second high-pressure carbamate condensation zone 4, and the non-condensed portion, if any, of the supplied gas mixture containing ammonia, carbon dioxide and water vapour, are passed into synthesis zone 1 via 36.

The gas liquid mixture obtained in the heat exchange in first high-pressure condensation zone 3 is passed via 37 into gas-liquid separator 8, from which the gas phase formed, a gas mixture containing ammonia, carbon dioxide and water vapour, is discharged via 38 and the liquid phase formed, a carbamate-containing urea solution, via 39.

In expansion valve 18, the liquid phase is reduced in pressure to the pressure of the second of the further decomposition stage, which normally is in the 1–10 bar range, for instance 5 bar, and the gas-liquid mixture formed during expansion is fed to gas-liquid separator 9. The stripped urea synthesis solution discharged from stripping zone 2 is also reduced in pressure to the pressure of the second of the further decomposition stages, for instance 5 bar, in expansion valve 19, and the gas-liquid mixture formed is fed to gas-liquid separator 9 via 40. Via 41, a urea-containing solution is discharged from gas-liquid separator 9, carbamate still present in this solution is decomposed in heat exchanger 10, which is heated by low-pressure steam, after which the urea solution is fed via 44 to heating zone 12 of the first concentration stage. Heating zone 12 may, for instance, be designed as a vertical tube heat exchanger, the urea solution to be concentrated being passed through the tubes. The gas phase obtained in gas-liquid separator 9, a gas mixture containing ammonia, carbon dioxide and water vapour, is discharged via 43 and passed, together with the gas mixture containing ammonia, carbon dioxide and water vapour that is obtained in heat exchanger 10 and discharged from it via 42, to low-pressure condensation zone 11 and condensed in this zone with an aqueous solution supplied via 54, for instance process condensate. The carbamate solution obtained in low-pressure condensation zone 11 is passed via 45 into the shell side of heating zone 12. This shell side is further fed with the gas mixture containing ammonia, carbon dioxide and water vapour that is obtained by joining streams 33 and 38, countercurrent to the urea solution to be concentrated. Supply of the carbamate solution preferably takes place at a point between the supply of the urea solution to be concentrated and the supply of the gas mixture to be condensed. Condensation in this way of the gas mixture by means of the carbamate solution supplied via 45 produces enough heat to meet the heat requirements of the first concentration stage, in which the urea solution supplied via 41, which contains 70–75 wt.% urea, is concentrated to a urea content of 85–95 wt.%. The carbamate solution formed in condensation of the gas mixture in the shell side of the heat exchanger of first concentration stage 12 is discharged via 46, brought up to synthesis pressure by means of carbamate pump 16, and introduced into scrubbing zone 5 via 47. The water vapour from the mixture of concentrated urea solution and water vapour that is discharged from the first concentration stage via 48 is separated via 49 in water vapour separator 14, while the concentrated urea solution is passed via 50 to the heating zone of second concentration stage 13. The mixture of virtually water-free urea melt and water vapour that is formed here is passed via 51 to water-vapour separator 15, from which via 52 the water vapour is discharged and via 53 the virtually water-free urea melt. The latter can, for instance be processed to granules or to a urea-ammonium nitrate solution. The water vapour from the concentration stages is condensed and the process condensate thus obtained can be treated in part or in its entirety in the customary manner to remove urea and ammonia and subsequently be discharged.

EXAMPLE

Using the process described, urea is prepared according to the embodiment represented in the FIGURE in a plant with three decomposition stages with a production capacity of 1000 tonnes a day. The amounts are given in kg an hour. The pressure applied in the high-pressure part of the plant is 139 bar, that in the second decomposition stage 21.5 bar and that in the last decomposition stage 5 bar. High-pressure condensation zone 3 is fed with 23,611 kg $NH_3$ of 40° C. and 41,647 kg of a carbamate solution with a temperature of 165° C., which contains 17,381 kg $CO_2$, 17,466 kg $NH_3$ and 6,790 kg $H_2O$. The temperature in reaction zone 1 is 183° C. and the $NH_3/CO_2$ molar ratio 3.2. Stripping zone 2 is fed with 68,202 kg urea synthesis solution, which solution is stripped with 16,530 kg $CO_2$ while heat is being supplied. Via 40, a solution containing 22,541 kg urea, 3,323 kg $CO_2$, 2,524 kg $NH_3$ and 10,146 kg $H_2O$ is discharged from the stripping zone, and via 25 a gas mixture consisting of 25,149 kg $CO_2$, 19,904 kg $NH_3$ and 1,145 kg $H_2O$. Contact zone 6 is fed with 54,092 urea synthesis solution, and this solution is treated here with 14,025 kg $CO_2$. From the bottom of contact zone 6, a solution is discharged that contains 19,222 kg urea, 11,562 kg $CO_2$, 10,619 kg $NH_3$ and 8,874 kg $H_2O$. From the top of this zone, a gas mixture is discharged that contains 10,949 kg $CO_2$, 6,407 kg $NH_3$ and 484 kg $H_2O$. The pressure of the solution discharged from contact zone 6 is subsequently reduced to 22 bar. As a result, in gas-liquid separator 7 4,234 kg is obtained of a gas mixture containing 2,715 kg $CO_2$, 1,375 kg $NH_3$ and 144 kg $H_2O$, which is discharged via 33. In addition, 46,043 kg remains of a liquid phase containing 19,221 kg urea, 8,847 kg $CO_2$, 9,244 kg $NH_3$ and 8,730 kg $H_2O$.

The gas mixture discharged from stripping zone 2 and contact zone 6 via 27 is in part condensed in first high-pressure condensation zone 3, yielding 86,169 kg of a carbamate solution. The residence time in this zone of the mixture is chosen such that also 17,234 kg urea is formed in this solution, which in addition contains 24,989 kg $CO_2$, 31,404 kg $NH_3$ and 12.543 kg $H_2O$. A further portion of the non-condensed gas mixture discharged via 34 is condensed in second high-pressure condensation zone 4, so that synthesis zone 1 is fed with a solution containing 34,336 kg $CO_2$, 42,702 kg $NH_3$, 13,126 kg $H_2O$ and 17,234 kg urea and with a gas mixture containing 6,506 kg $CO_2$, 14,831 kg $NH_3$ and 463 kg $H_2O$.

In first high-pressure condensation zone 3 the heat released is discharged by means of liquid stream 32, resulting in decomposition into $NH_3$ and $CO_2$ of carbamate present in this stream. After the reaction mixture thus obtained has been subjected to a gas-liquid separation, at a pressure of 21.5 bar and a temperature of 159° C., via 38 a gas stream is obtained that consists of 7,861 kg $CO_2$, 6,616 kg $NH_3$ and 1,546 kg $H_2O$, and via 39 a solution which, besides 19,126 kg urea, contains 1,056 kg $CO_2$, 2,684 kg $NH_3$ and 7,156 kg $H_2O$. This solution and the solution discharged from stripping zone 2 are expanded to a pressure of 5 bar and the mixtures obtained are passed into gas-liquid separator 9. Via 43, a gas mixture consisting of 2,805 kg $CO_2$, 2,308 kg $NH_3$ and 1,081 kg $H_2O$ is passed to condensation zone 11. The solution discharged via 41, which contains 41,667 kg urea, 1,574 kg $CO_2$, 2,900 kg $NH_3$ and 16,221 kg $H_2O$, is heated to 130° C. in heater 10. This yields, via 42, a gas mixture containing 872 kg $CO_2$, 882 kg $NH_3$ and 520 kg $H_2O$. For the condensation of the gas mixtures fed to low-pressure condensation zone 11 via 42 and 43, via 54 5,920 kg process condensate containing 702 kg $CO_2$ and 2,018 kg $NH_3$ is supplied. After expansion in expansion valve 20, the urea solution obtained via 44, which consists of 41,667 kg urea, 702 kg $CO_2$, 2,018 kg $NH_3$ and 15,701 kg $H_2O$ and has a temperature of 130° C., is passed to heating zone 12 of the first concentration stage. The heat required for concentrating is obtained by condensing the combined gas streams 33 and 38 in the shell side of heating zone 12, use being made of the carbamate solution obtained in the low-pressure stage and supplied via 45, which contains 4,379 kg $CO_2$, 5,208 kg $NH_3$ and 4,802 kg $H_2O$ and has a temperature of 63° C. From heating zone 12, a gas-liquid mixture is discharged to gas-liquid separator 14, from which, at a pressure of 0.38 bar and a temperature of 130° C., via 50 43,871 kg urea solution in water is obtained, which contains 41,667 kg urea, 2,193 $H_2O$ and traces of $NH_3$.

Stripping zone 2 is fed with 20,300 kg steam of 23.5 bar and 221° C., which corresponds with 487 kg per tonne of urea produced. In second high-pressure condensation zone 4 17,800 kg low-pressure steam of 5 bar is produced. Of this, 2,600 kg is utilized in heat exchanger 10 and 2,630 kg in heating zone 13 of the second concentration stage. The remaining amount is used for maintaining, by means of steam ejectors, the required vacuum in water vapour separators 14 and 15 in the wastewater purification plant (not shown).

I claim:

1. In a process for the preparation of urea from the reaction of ammonia and carbon dioxide at an $NH_3/CO_2$ molar ratio of up to about 4:1 in a high pressure synthesis zone maintained at a temperature of between about 175° and 220° C. and a synthesis pressure of between about 125 and 250 bar, to form a urea synthesis solution containing unconverted ammonium carbamate and excess ammonia, wherein in a first decomposition stage, a portion of the unconverted ammonium carbamate present in said urea synthesis solution is decomposed to ammonia and carbon dioxide at a pressure of at most the pressure in said high pressure synthesis zone by the simultaneous supply of heat and countercurrent contact with a carbon dioxide stripping gas, and separately removing therefrom a first decomposition stage gas mixture containing ammonia, carbon dioxide and water vapor, and a residual urea solution still containing unconverted ammonium carbamate, in a first condensation stage, said first decomposition stage gas mixture is at least in part condensed to form a first condensate which, together with any remaining noncondensed gas mixture, is returned to the synthesis zone, in at least two further decomposition stages, residual urea solution is heated, thereby decomposing further portions of said ammonium carbamate, and the gas mixtures thereby formed are separated from the residual urea solutions and condensed, the first of said further decomposition stages being maintained at a pressure of between about 12 and 30 bar, and the second of said further decompositions stages being maintained at a pressure lower than the pressure in the first of said further decomposition stages, whereafter in a concentration stage, the remaining urea-containing solution is concentrated to product urea by evaporation of water, the improvement essentially comprising dividing said urea synthesis solution into first and second portions for separate treatment in said first decomposition stage wherein said first portion of urea synthesis solution is subjected to a stripping treatment with carbon dioxide while heat is being supplied, thereby forming a first gas mixture and a first residual urea solution, said second portion of urea synthesis solution is countercurrently contacted with carbon dioxide under adiabatic conditions, thereby forming a second gas mixture and a second residual urea solution, said first and second gas mixtures are combined as said first decomposition stage gas mixture and at least in part condensed in said first condensation stage, said first residual urea solution is supplied to the second of said further decomposition stages, and said second residual urea solution is supplied to the first of said further decomposition stage.

2. The process of claim 1 wherein said first portion is 50–70 wt.% of said urea synthesis solution from the high pressure synthesis zone.

3. The process of claim 1 wherein said second residual urea solution, after expansion and separation of a third gas mixture containing ammonia and carbon dioxide released upon said expansion, is supplied to said first further decomposition stage wherein a further amount of ammonium carbamate still present in said second residual urea solution is decomposed utilizing the heat released by condensation of the first decomposition stage gas mixture in said first condensation zone, thereby forming a fourth gas mixture containing ammonia and carbon dioxide which is separated from the residual urea solution.

4. The process of claim 3 wherein said third gas mixture is condensed together with said fourth gas mixture by indirect heat exchange with the remaining urea solution to be concentrated, and the condensate thus formed is returned to the high pressure synthesis zone.

* * * * *